United States Patent [19]
Reisner

[11] Patent Number: 5,858,328
[45] Date of Patent: Jan. 12, 1999

[54] ANIMAL MODEL FOR HEPATITIS VIRUS INFECTION

[75] Inventor: Yair Reisner, Tel Aviv, Israel

[73] Assignee: Yeda Research and Development Co. Ltd., Rehovot, Israel

[21] Appl. No.: 337,925

[22] Filed: Nov. 10, 1994

Related U.S. Application Data

[63] Continuation-in-part of Ser. No. 242,580, May 13, 1994, and a continuation-in-part of Ser. No. 61,706, May 17, 1993, Pat. No. 5,652,393, which is a continuation-in-part of Ser. No. 892,911, Jun. 2, 1992, abandoned, said Ser. No. 242,580, is a continuation-in-part of Ser. No. 61,706.

[30] Foreign Application Priority Data

Jun. 14, 1991 [IL] Israel .......................................... 98369
Sep. 8, 1993 [IL] Israel ........................................ 106951

[51] Int. Cl.$^6$ .......................... A61K 49/00; C12N 15/00; G01N 31/00
[52] U.S. Cl. ......................... 424/9.2; 424/9.1; 435/172.3; 800/2
[58] Field of Search ................................. 800/2; 427/9.1, 427/9.2, 93.21, 93.1, 93.2, 558, 553, 550, 551; 435/172.3

[56] References Cited

U.S. PATENT DOCUMENTS

| | | |
|---|---|---|
| 4,683,200 | 7/1987 | Hirohashi et al. . |
| 5,147,784 | 9/1992 | Peault . |

FOREIGN PATENT DOCUMENTS

| | | |
|---|---|---|
| 0 322 240 | 6/1989 | European Pat. Off. . |
| 0438053 | 7/1991 | European Pat. Off. . |
| 0469632 | 2/1992 | European Pat. Off. . |
| 0517199 | 12/1992 | European Pat. Off. . |
| 89/12823 | 12/1989 | WIPO . |
| 91/16451 | 10/1991 | WIPO . |
| 91/16910 | 11/1991 | WIPO . |
| 91/18615 | 12/1991 | WIPO . |
| 92/03918 | 3/1992 | WIPO . |
| 92/06715 | 4/1992 | WIPO . |

OTHER PUBLICATIONS

Barry, et al, "Successful Engraftment of Human Postnatal Thymus in Severe Immune Deficient (SCID) Mice: Differential Engrafment of Thymic Components with Irradiation Versus Anti–asialo GM–1 Immuno–Suppressive Regimens", *J. Exp. Med.,* 173:167–180 (1991).

Bosma, et al, "A Severe Combined Immunodeficiency Mutation in the Mouse", *Nature* 301:527–531 (1983).

Giovanella, et al, "Heterotransplantation of Human Cancers into Nude Mice", *Cancer,* 42:2269–2281 (1978).

Kamel–Reid, et al, "Engrafment of Immune–Deficient Mice with Human Hematopoietic Stem Cells", *Science,* 242:1706–1708 (1988).

Kamel–Reid, et al, "A Model Human Acute Lymphoblastic Leukemia in Immune–Deficient SCID Mice", *Science,* 246:1597–1600 (1989).

Keever, et al, "Immune Reconstitution Following Bone Marrow Transplantation: Comparison of Recipients of T–Cell Depleted Marrow With Recipients of Conventional Marrow Grafts", *Blood,* 73:1340 (1989).

McCune, et al, "The SCID–hu Mouse: Murine Model for hte Analysis of Human Hematolymphoid Differentiation and Function", *Science,* 241:1632–1639 (1988).

McCune, et al, "Pseudotypes in HIV–Infected Mice", *Science,* 250:1152–1154 (1990).

Miyami–Inaba, et al, "Isolation of Murine Pluripotent Hematopoietic Stem Cells in the Go Phase", *Biochemical and Biophysical Research Communications,* 147(2):687–695 (1987).

Mosier et al, "Transfer of a Functional Human Immune System to Mice with Severe Combined Immunodeficiency", *Nature,* 225:256–259 (1988).

Murphy, et al, "An Absence of T Cells in Murine Bone Marrow Allografts Leads to an Increased Susceptibility to Rejection by Natural Killer Cells and T Cells", *Journal of Immunology,* 144:3305–3311 (1990).

Namikawa, et al, "Infection of the SCID–hu Mouse by HIV–1", *Science,* 242:1684–1686 (1988).

Namikawa, et al, "Long–Term Human Hematopoiesis in the SCID–hum Mouse", *J. Exp. Med.,* 172:1055–1063 (19990).

Reisner, et al, "Transplantation for Severe Combined Immunodeficiency with HLA–A, B, D, DR Incompatible Parental Marrow Cells Fractioned by Soybean Agglutinin and Sheep Red Blood Cells", *Blood,* 61:341 (1983).

Schuler, et al, "Rearrangement of Antigen Receptor Genese in Defective Mice with Severe Combined Immune Deficiency", *Cell,* 46:963–972 (1986).

*Stedman's Medical Dictionary,* 24th ed., Williams & Wilkins, Baltimore, 1982, p. 1242.

Sykes, et al, "Mixed Allogeneic Chimerism as an Approach to Transplantation Tolerance", *Immunology Today,* 9(1):23–27 (1988).

van Bekkum, et al, "Immune Reconstitution of Radiation Chimeras", *Bone Marrow Transplantation: Biological Mechnisms and Clinical Practice,* Dekker, New York, pp. 311–350.

(List continued on next page.)

*Primary Examiner*—Brian R. Stanton
*Attorney, Agent, or Firm*—Browdy and Neimark

[57] ABSTRACT

A non-human chimeric animal is obtained by transplanting a non-human mammal host having a T cell deficiency with a human liver tissue preparation or with a liver tissue preparation from a non-human animal capable of being infected by the hepatitis virus (HV). The non-human chimeric animal is useful as an HV model for evaluating anti-HV therapy and prophylaxis.

12 Claims, 6 Drawing Sheets

OTHER PUBLICATIONS

Galun, E., et al., "Hepatitis C Viremia in Chimeric Mice", *Hepatology,* vol. 20, No. 4/2, p. 232A, Oct. 1994, 45th Annual Meeting of the American Association for the Study of Liver Diseases, Nov. 11–15, 1994.

Lubin, I., et al., "Engrafment and Development of Human T and B Cells in Mice After Bone Marrow Transplantation", *Science,* vol. 252, pp. 427–431, 19 Apr. 1991.

Lubin, I., et al., "Engrafment of Human Peripheral Blood Lymphocytes in Normal Strains of Mice", *Blood,* vol. 83, No. 8, pp. 2368–2381, 15 Apr. 1994.

Mosier, D.E., "Adoptive Transfer of Human Lymphoid Cells to Severely Immunodeficient Mice: Models for Normal Human Immune Function, Autoimmunity, Lymphomagenesis, and AIDS", *Advances in Immunology,* vol. 50, pp. 303–325, 1991.

Nakamura, T., et al., "Successful Liver Allografts in Mice by Combination with Allogeneic Bone Marrow Transplantation", *PNAS,* vol. 83, pp. 4529–4532, Jun. 1986.

Shimizu, Y.K., et al., "Correlation Between the Infectivity of Hepatitis C Virus In Vivo and Its Infectivity In Vitro", *PNAS,* vol. 90, pp. 6037–6041, Jul. 1993.

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:1:

CACTCCACCA TAGATCATCC C        21

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:2:

ACCACTACTC GGCTAGCAGT        20

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:3:

TTCACGCAGA AAGCGTCTAG        20

( 2 ) INFORMATION FOR SEQ ID NO:4:

-continued (i) SEQUENCE CHARACTERISTICS:
  (A) LENGTH: 20 base pairs
  (B) TYPE: nucleic acid
  (C) STRANDEDNESS: single
  (D) TOPOLOGY: linear (ii) MOLECULE TYPE: DNA (xi) SEQUENCE DESCRIPTION: SEQ ID NO:4:

GTTGATCCAA GAAAGGACCC                                                                                          20

ANIMAL MODEL FOR HEPATITIS VIRUS INFECTION

CROSS REFERENCE TO RELATED APPLICATIONS

The present application is a continuation-in-part of U.S. patent application Ser. No. 08/242,580, filed on May 13, 1994, and a continuation-in-part of application Ser. No. 08/061,706, filed May 17, 1993, now U.S. Pat. No. 5,652,393, which is a continuation-in-part of application Ser. No. 07/892,911 filed Jun. 2, 1992, now abandoned. Said application Ser. No. 08/242,580 is also a continuation-in-part of said application Ser. No. 08/061,706.

FIELD OF INVENTION

The present invention concerns an animal model for hepatitis virus (HV) infection in humans, particularly hepatitis B virus (HBV) and hepatitis C virus (HCV) infection.

PRIOR ART

The following is a list of prior art and references considered to be pertinent for the description below:

1. Choo, Q-L, Kuo G, Weiner, A. J. Overby L. R., Bradley D. W., Houghton, M. Isolation of cDNA clone derived from a blood-borne non-A, non-B viral hepatitis genome. 1989. *Science* 244:359–362.
2. Kuo G, Choo Q-L, Alter H. J., Gitnick, G. L., Redeker A. G., Purcell R. H., Miyamura T, Dienstag J. L., Alter H. J. Stevenes C. E., Tegtmeier G. E., Bonnino F., Colombo M, Lee W-S, Kuo C, Berger K, Shuster J. R., Overby L. R., Bradley D. W., Houghton M. 1989. An essay for circulating antibodies to major etiologic virus of human non-A, non-B hepatitis. *Science* 244:362–344.
3. Prince, A. M., Brotman B., Huima T., Pascual D., Jaffery M. Inchauspe G. 1992. Immunity in hepatitis C infection. *J. Infec. Dis.* 165:438–443.
4. Shimizu Y. K., Weiner, J. Rosenblatt J., Wong D. C., Shapiro M., Popkin T, Houghton M, Alter H. J., Purcell R. H. 1990. Early events in hepatitis C virus infection in chimpanzees. *Proc. Natl. Acad. Sci.* (USA) 87:6441–6444.
5. Shimizu, Y. K., Iwamoto A., Hijikata M., Purcell R. H., Yoshikura H. 1992. Evidence for in vitro replication of hepatitis C virus genome in a human T cell line. *Proc. Natl. Acad. Sci.* (USA) 89:5477–5481.
6. Shimizu Y. K., Purcell R. H., Yoshikura H. 1993. Correlation between the infectivity of hepatitis C virus in vivo and its infectivity in vitro. *Proc. Natl. Acad. Sci.* (USA) 90:6037–6041.
7. Nakamura T., Good R. A., Yasumizu R., Inoue S., Oo M. M., Hamashima Y, Ikehara S. 1986. Successful liver allografts in mice by combination with allogeneic bone marrow transplantation. *Proc. Natl. Acad. Sci.* (USA) 83:4529–45326.
8. Bosma, M. J. Carroll, A. M. 1991. The SCID mouse mutant: Definition, characterization, and potential uses. *Annu. Rev. Immunol.* 9:323–350.
9. Soriano, H. E., Adams, R. M., Darlington G., Finegold M. Steffen D. L., Ledley F. D. 1992. Retroviral transduction of human hepatocytes and orthotopic engraftment in SCID mice after hepatocellular transplantation. *Trans. Proc.* 24:3020–3021.
10. Aldrovandi G. M., Feurer G., Gao L., Jamieson B., Kristeva M., Chen I. S. Y., Zack J. A., 1993. The SCID-hu mouse as a model for HIV-1 infection. *Nature* 363:732–736.
11. European laid open Patent Application, Publication No. 438053.
12. European laid open Patent Application, Publication No. 517199.

The citation herein of the above publications is given to allow an appreciation of the prior art. This citation should not, however, be construed as an indication that this art is in any way relevant to the patentability of the invention, as defined in the appended claims.

The above publications will be acknowledged herein by indicating their number from the above list.

BACKGROUND OF THE INVENTION

Five different viruses have been identified as causes of viral hepatitis. These include hepatitis A, B, C, D and E viruses. Of these, the viruses which cause the most serious infections are hepatitis B virus (HBV) and hepatitis C virus (HCV).

Hepatitis A virus has a single serotype and causes a self-limited acute infection. A large percentage of the population, approaching 50%, has hepatitis A antibodies in serum and is probably immune to disease. Infection with hepatitis A does not progress to chronic disease.

HBV is implicated in both acute and chronic hepatitis. The disease is endemic in Asia, is increasing in prevalence in the U.S. and Europe. Chronic liver disease, resulting in significant morbidity and increased mortality, is sequela of infection in 1–10% of infected individuals. HBV infection is also correlated with the development of primary liver cancer.

HCV was recently shown to be the major causative agent of parenterally transmitted non-A, non-B hepatitis[1]. It is estimated that 0.5–1% of the world population is infected with HCV, and in some developing countries the prevalence rate is up to 40%. Moreover, 40–60% of newly infected patients develop persistent HCV infections[2] and are at risk of developing acute, fulminant hepatitis and various chronic liver diseases (including cirrhosis, chronic active hepatitis and in some cases hepatocellular carcinoma).

Hepatitis D virus ("Delta Virus") is a defective RNA virus that can only infect the liver in the presence of an active HBV infection. Hepatitis E virus appears to be a single-stranded RNA virus. Infection with hepatitis E virus is not known to progress to chronic liver disease.

Although HBV and HCV have been identified and characterized, the development of new anti-viral strategies has been greatly hampered by the lack of adequate, simple and low cost animal model systems.

Currently, biological assays for HBV and HCV have been limited to the experimental inoculation of chimpanzees[3,4], which are expensive and limited in numbers. In addition, an in vitro system for the propagation of HCV was developed in the murine retrovirus infected human T cell lines, HPB-Ma[5] and Molt4-Ma[6], in which replication of HCV is achieved.

It has recently been demonstrated in several studies that human solid organs such as fetal thymus or fetal liver as well as several types of tumors were successfully grafted into SCID mice under the kidney capsule[7]. In addition, transplantation of other organs such as lymph nodes and bone marrow spicules and engraftment of organs to other sites (i.e. subcutane and peritoneum) have also been reported.

A SCID mouse mutant was reported to support human cell implantation, i.e. single hepatocyte transplantation[8,9], and was also used as a model for human infectious diseases, i.e. HIV-1 infections[10].

It has been disclosed that lethally irradiated mice, radio-protected with bone marrow from SCID mice, developed marked immune-deficiency and supported engraftment of human peripheral blood lymphocytes (PBL) for a long period of time[11]. It was also disclosed that human implants of non-hematopoietic origin were accepted and maintained for prolonged periods of time after transplantation under the kidney capsules of these chimeras[12].

GENERAL DESCRIPTION OF THE INVENTION

It is an object of the present invention to provide a convenient non-human animal model for HV infection.

It is further an object of the present invention to provide a method for evaluation of preventive and therapeutic agents for the treatment and prophylaxis of HV infections using the above non-human animal model.

It is still another object of the present invention to provide methods for production of anti-HV antibodies or T cells, and particularly human monoclonal antibodies and cytotoxic T cells, using chimeric non-human mammals transplanted with human hematopoietic cells and human liver tissue infected by HV either pre- or post-transplant.

The present invention is based on the realization that an animal having a T cell deficiency, transplated with human liver tissue, or liver tissue from a non-human mammal capable of being infected by HV, can be used very effectively as an HV model. The model of the invention is very useful for a variety of applications including screening of drugs for anti-HV effect and development of vaccines and other prophylactic anti-HV agents. Furthermore the chimeric mammals in accordance with the invention can also be used for the production of anti-HV antibodies or T cells.

The present invention thus provides, by a first of its aspects, a non-human chimeric animal obtained by transplanting a non-human mammal having a T cell deficiency with a human liver tissue preparation or with a liver tissue preparation from a non-human animal capable of being infected by HV.

For a variety of applications, such as for the purpose of producing anti-HV antibodies or anti-HV cytotoxic T cells, which will be elaborated further below, said non-human mammal host may at times be inoculated with stem cells or lymphocytes from another mammalian species, e.g. human, which may lead to the development, in said chimeric mammals, of functional B and T cells of the other species. Then, upon infection of said mammals with HV, cell lineages, reactive against HV (both of the B and T lineages) will develop in said chimeric mammals.

For use as an animal model, said non-human mammal host may either be transplated with an a priori HV-infected liver tissue preparation, or in the alternative, the transplanted liver tissue may be infected in vivo after transplantation. A model of the former type is particularly useful for evaluating therapeutic agents for the treatment of acute HV infection, and a model of the latter type is particularly useful for evaluating prophylactic agents, e.g. vaccines.

The non-human mammal host which has a T cell deficiency, may for example be a mammal having a genetic T cell deficiency, i.e. a mammal carrying a genetic trait whereby functional T cells are not produced or produced to a very limited extent. Particular examples of such animals are severe combined immuno deficient (SCID) mice, nude mice, beige/nude/Xad (BNX) mice, etc.

Other examples of hosts useful for transplantation of liver tissue preparations so as to obtain the above chimeric mammal, are animals having an induced T cell deficiency. Induction of such deficiency may be by the administration to the host of an agent specifically active in destroying functional T cells, such as anti-CD4 or anti-CD8 antibodies.

A preferred host in accordance with the invention is a host which is made to be substantially T Cell deficient by first destroying its hematopoietic system and then transplanting it with a hematopoietic cell preparation from a mammal having a genetic T cell deficiency or with a T cell depleted mammalian stem cell or bone marrow preparation.

In accordance with the above preferred embodiment, the present invention provides a non-human chimeric animal, comprising a mammal M5 having xenogeneic cells; mammal M5 being derived from a mammal M1 treated to substantially destroy its hematopoietic cells and then transplanted with hematopoietic cells derived from one or more mammals M2 and transplanted with liver tissue from a mammal M3, the one or more mammals M2 and mammal M3 being from the same or from a different species; the transplanted hematopoietic cells from the one or more mammals M2 being either one or both of a hematopoietic cell preparation from a T cell deficient mammal or of a T cell depleted mammalian stem cell or bone marrow preparation; the transplanted liver tissue from mammal M3 being either a human liver tissue preparation or a liver tissue preparation from a non-human mammal capable of being infected by HV; the liver tissue preparation in the M5 mammal being infected by HV.

For some applications, e.g. for raising anti-HV immune cells or antibodies, mammal M5 may also be transplanted with a hematopoietic preparation from a mammmam M6 from a species other than M1 or M2, e.g. human, which may be a T cell depleted stem cell enriched preparation or peripheral blood lymphocytes (PBL).

The non-human mammal host in general, and the M1 mammal in accordance with the preferred embodiment in particular, may typically be a mouse or a rat, although the animal host may also be a non-human mammal of a higher order such as a primate, e.g. a marmoset monkey.

For the obtaining of an M5 mammal from said M1 mammal, the M1 mammal is first treated in a manner so as to substantially destroy its hematopoietic system. The term "substantially destroyed" should be understood as meaning that the number of hematopoetic cells which survive following the treatment are insufficient to immune-protect the animal in the absence of the transplant from the M2 mammal. Following treatment intended to substantially destroy the hematopoietic cells, some such cells survive but the number is small such that the animal could not survive under normal laboratory conditions.

A treatment intended to substantially destroy the hematopoietic cells may, for example, be a split dose total body irradiation, (TBI). A TBI effective in destroying the hematopoietic system requires typically an accumulative dosage of 4–50 Gy (1 Gy=100 rad). In the case of a mouse, the irradiation may, for example, be a 4 Gy on day 1 and 9–15 Gy three days later. A similar irradiation dose was found to be effective in destroying the hematopoietic cells also in rats and marmoset monkeys.

M2 is preferably a mammal of a species either the same of the M1 mammal or a closely related species. The term "related species" means to denote a species which is taxonomically related to the M1 species. For example, where M1 is a mouse, M2 may either be a mouse, a rat or some other rodent. Particularly preferred in accordance with the invention for use as an M2 donor is a severe combined immunodeficient (SCID) mouse or a SCID animal of another rodent species. The transplanted hematopoietic cell preparation in this case is suitably a bone marrow prepration. The transplanted hematopoietic cells derived from the M2 mammal may also be a T cell depleted hematopoietic stem cell preparation obtained from a donor M2 mammal.

The hematopoietic preparation from mammal M6 may be obtained from a variety of mammals, such as primates, e.g. humans. In the case of humans, a stem cell enriched preparation may, for example, be obtained from peripheral blood of donors pretreated with a granulocyte colony stimulating factor (G-CSF) or from cancer patients undergoing chemotherapy known to cause migration of stem cells to the periphery. After withdrawal of the blood preparation from such donors, the preparation is typically treated to remove various blood components and to deplete the T cells therefrom. For T cell depletion, the M6 derived hematopoietic cell preparation may be subjected to treatment intended for enrichment with cells displaying the CD34 antigen (CD34$^+$ cells). Each of the above stem cell enriched, T cell depleted preparations can either be used directly after their withdrawal from the donor, or may be a cell-preparation which underwent one or a plurality of passages in vitro. PBL's from human and other M6 mammals may be obtained by electrophoresis, as known per se.

In order to obtain the M5 mammal, the M1 mammal may be transplanted with an HV infected liver tissue. Such an HV infected liver tissue may be obtained from an M3 mammal infected with HV, e.g. a liver biopsy from an HV infected human. Furthermore, an HV infected liver tissue preparation may also be obtained by in vitro infection of an a priori non-HV infected liver tissue preparation obtained from a non-HV infected M3 donor mammal. Alternatively, rather than transplanting the M1 mammal with an HV infected liver tissue, the M1 mammal may first be transplanted with liver tissue not infected by HV, thus obtaining an M4 mammal, and then inoculating the M4 mammal with HV leading to infection of the transplanted liver tissue.

An M4 mammal may thus serve as a model for testing the efficacy of an agent in the prophylaxis of HV. In such a model, the putative prophylactic agent is administered to the M4 mammal either prior or together with the HV and its ability to inhibit HV infection can then be determined.

In addition to human liver tissue preparation, it is also possible to use liver tissue preparations from non-human M3 mammals susceptible to HV infections such as chimpanzees or other non-human primates.

The animal model of the invention is particularly suitable for the study of the pathology of HBV and HCV infections and the development of therapies therefor. Models for both HBV and HCV are particularly preferred in accordance with the invention, as no simple and low cost models for these viral infections are currently available.

The invention further provides, by a second of its aspects, a method for evaluating the potential of an agent or a combination of agents in the therapy of an HV infection, comprising:

(a) providing a chimeric mammal as defined above;
(b) administering said agent or said combination of agents to said mammal; and
(c) evaluating the effectiveness of said agent or said combination of agents in preventing spread of HV infection, reducing its physiological symptoms or reducing the evidence of active infection in said M5 mammal.

Said chimeric mammal in accordance with the second aspect, is preferably a mammal M5 as defined above.

The present invention still further provides, by a third of its aspects, a method for evaluating the potential of an agent or a combination of agents, in the prevention of an HV infection, comprising:

(a) providing said chimeric mammal having transplanted therein a non-HV infected liver tissue preparation;
(b) administering said agent or said combination of agents to said M4 mammal;
(c) infecting said mammal with HV; and
(d) evaluating the effectiveness of said agent or said combination of agents in preventing primary HV infection of the liver tissue of said mammal.

Said chimeric mammal in accordance with the third aspect is preferably a mammal M4 as defined above.

By a modification thereof, the methods according to the second or third aspects, may also be applied in determining the effective dose of said agent or said combination of agents in therapy or prevention of the HV infection, as the case may be.

By a fourth of its aspects, the present invention provides a method for obtaining anti-HV immune cells or antibodies of a species other than said non-human mammal host comprising:

(a) providing said chimeric mammal comprising stem cells or lymphocytes of a species other than said non-human mammal host;
(b) recovering immune cells or antibodies from said chimeric mammals; and
(c) selecting for said cells or said antibodies being of said species origin having an anti-HV reactivity.

Optionally, said chimeric mammal, in accordance with the fourth aspect, which is preferably an M5 mammal having the derived lymphocytes as stem cells, is treated so as to increase the immune response against HV, such as for example by vaccination.

Said immune cells may be antibody producing B cells or be T cells. Anti-HV antibody producing B cells may be immortalized to obtain live secreting anti-HV monoclonal antibodies. The anti-HV antibodies produced in accordance with the fourth aspect may be used as therapeutic agents in anti-HV therapies of hepatitis patients.

The manner of immortalization of B cells to produce B cell lines, as well as the manner of selecting immortalized B cell lines to obtain those having the desired reactivity, is generally known per se and the full explanation of such methods goes beyond the present writing.

The invention will now be described with reference to some specific embodiments described in the following examples and the appended drawings.

EXAMPLES

Figure 1A:
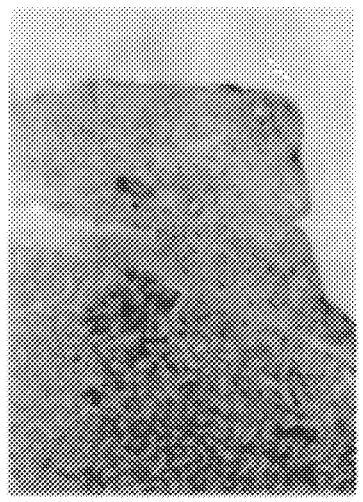
FIGS. 1A–1C show histology of liver tissue transplanted under the kidney capsule of SCID-BNX chimera, 1 month after transplantation of liver fragments from BNX mouse (A), Lewis rat (B), or human (C). All transplanted animals which survived the kidney subcapsular implantation of liver tissue were assessed for engraftment by light microscopy of the kidneys using H&E staining.

Example 1
Engraftment of Human Liver Segment from non-HCV Patients

BNX mice (6–10 weeks old, female) were purchased from Harlam Sprague-Dawley (Indianapolis, Ind.) and CB17/SCID mice were from the Animal Breeding Center, Weizmann Institute, Rehovot, Israel. Mice were kept in small cages (5 animals in each cage) and fed sterile food and acid water containing cyprofloxacin (20 mg/ml). Prior to transplantation, the BNX mice were conditioned with 12 Gy TBI and radioprotected the following day with 2–3×10$^6$ T cell depleted SCID bone marrow cells. TBI was administered from a gamma beam 150-A $^{60}$Co source (Atomic Energy of Canada, Kanata, Ontario) with F.S.D. of 75 cm and a dose rate of 0.7 Cy/min. Bone marrow cells obtained from SCID mice (4–10 weeks old) were fractionated by differential agglutination with soybean agglutinin (to remove T lymphocytes that may be present in occasional "leaky" SCID mice) as previously described[11]. One day after bone marrow transplantation, human, rat or mouse liver fragments were grafted under the kidney capsule.

Rat and mouse liver tissue fragments were collected through laparotomy, in which a wedge biopsy was cut from the animal liver and kept under sterile conditions at 4° C., in Dulbecco modified Eagle medium containing 10% fetal calf serum or ViaSpan (Belzer UW solution, Du Pont Pharmaceuticals, Hertogenbosch, The Netherlands).

Human liver segments were obtained during hepatic segmentectomy when performed for primary or secondary liver tumors. In all cases, the non-tumor tissue was non-cirrhotic, as confirmed by hematoxylin and eosin (H&E) staining. The liver segments were kept, for up to 2 hours in UW solution prior to transplantation. For engraftment of liver tissue, BNX mice were anesthetized with Nembutol or Avertin. An incision of approx. 1 cm was then made in the right or left flank, the kidney was exposed and liver tissue (cut into 1 mm$^2$ pieces) was placed under the renal capsule using fine forceps. One suture was placed to close the wound. Kidneys, with the attached transplanted tissue, were removed at various time intervals (from 8 days to 3 months), fixed in Bouin's liquid, embedded in paraffin, and 4 μm sections were stained with H&E.

A summary of the transplantations of liver fragments in the SCID-BNX chimeric mice is shown in the following Table 1.

TABLE 1

| Number of Mice | | | | Follow-up |
|---|---|---|---|---|
| Transplanted | Surviving | Engrafted | Source of liver | (weeks) |
| 10 | 9 | 4 | Mouse | 10 |
| 20 | 12 | 8 | Mouse | 3 |
| 10 | 7 | 4 | Mouse | 1.4 |
| 10 | 10 | 8 | Rat | 10 |
| 20 | 8 | 5 | Rat | 8 |
| 20 | 7 | 2 | Rat | 2 |
| 10 | 5 | 2 | Rat | 1.4 |
| 20 | 11 | 5 | Human | 14 |
| 20 | 11 | 5 | Human | 14 |
| 20 | 11 | 5 | Human | 12 |
| 20 | 10 | 2 | Human | 6 |
| 20 | 9 | 3 | Human | 4 |
| 20 | 16 | 12 | Human | 2 |
| 20 | 15 | 14 | Human | 2 |
| 16 | 12 | 9 | Human | 2 |

As seen from the above table, the survival rate of the chimeric mice receiving the human liver graft was at the order of about 50–60%.

Figure 1B:
Figure 1C:
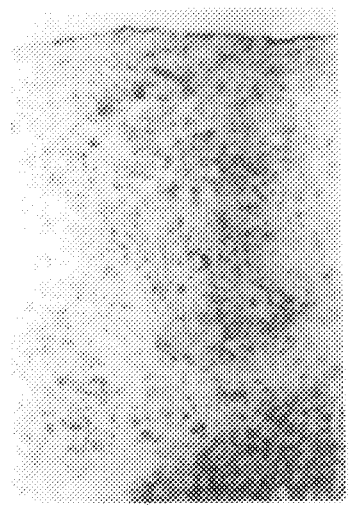
Figure 2A:
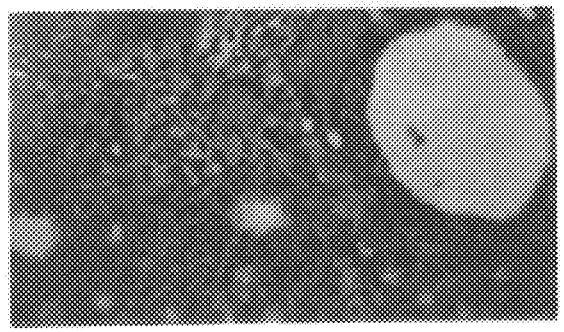
FIGS. 2A–2C show hepatocytes and bile duct-like structures (marked with arrows) in a transplanted human liver fragment 30 days after grafting at ×240 magnification (A); hepatocytes and epithelial cells at ×1200 magnification (B), bile duct-like structures at ×1200 magnification (C).
Figure 2B:
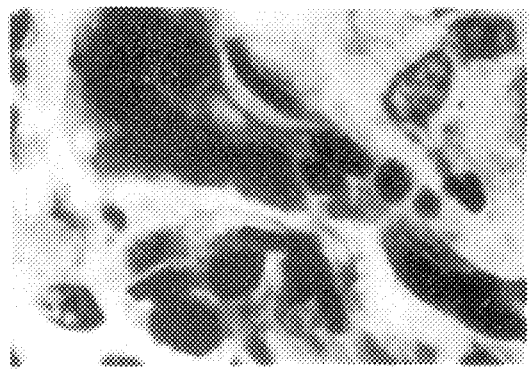
Figure 2C:

Histological examination of the transplanted liver fragments at this subcapsular area of the transplanted SCID-BNX chimera showed that following transplantation, the typical liver cell architecture disappeared and, in most transplants, central ischemia occurred while the peripheral tissue of the transplant was markedly fibrotic (see FIG. 1). In most cases, hepatocytes were recognized in addition to proliferating epithelial cells (FIG. 2) and the engrafted tissue mainly resembled the morphological characteristics of biliary epithelium (FIGS. 2B and 2C). A very mild inflammatory reaction was occasionally observed consisting a few polymorphonuclear and plasma cells.

Evaluation of liver engraftment rate showed that among the mice receiving the human liver grafts, 15 out of 33 retained the graft for more than 12 weeks while 40 out of 62 were stably engrafted at six weeks or less (Table 1).

Example 2
Transplantation of Liver Tissue from a human infected with hepatitis B virus (HBV)

Figure 3A:
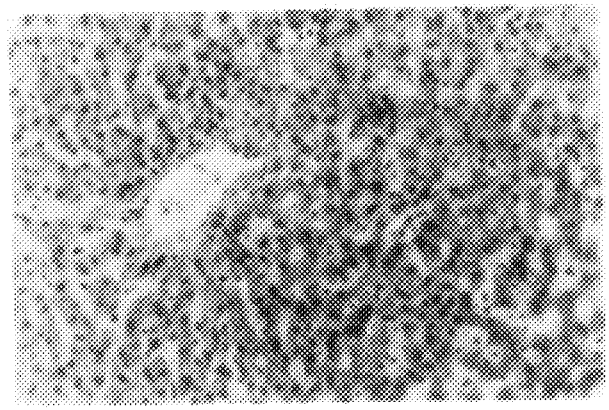
FIGS. 3A–3D show (A) histology of a liver segment prior to transplantation (H&E, ×100) (B), immunohistological staining for HBsAg of human liver, infected with HBV (×100) (C), periodic acid-Schiff staining for glycogen of a human liver (L) segment transplanted under the kidney (K) capsule of a SCID-BNX chimera (×50) and (D), immunohistological staining for HBsAg of human liver infected with HBV, as observed 19 days after transplantation at the subcapsular area of the SCID-BNX chimera kidney (×50). Staining was performed using, as a primary antibody, mouse anti-HBsAg (Zymed Lab, San Francisco, Calif.).
Figure 3B:
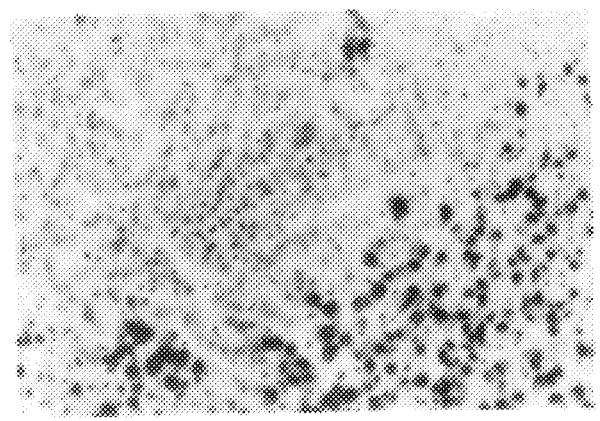
Figure 3C:
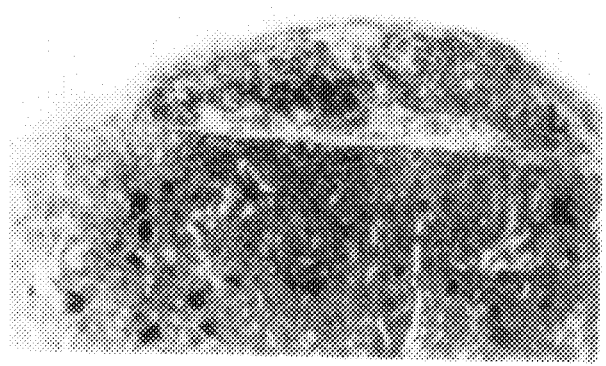
Figure 3D:
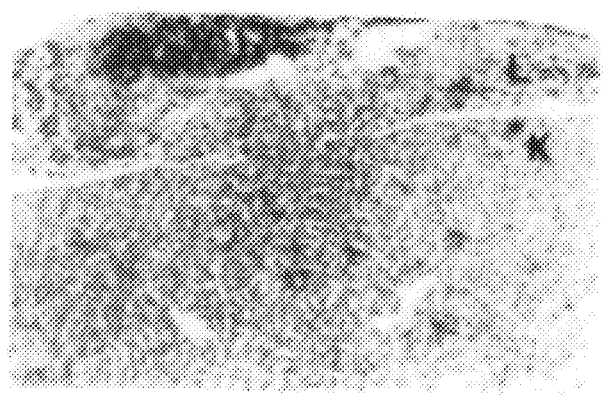

A liver biopsy from a patient infected with hepatitis B virus (HBV) was obtained and transplanted under the kidney capsule of SCID/BNX chimera mice as described in Example 1. Immunohistology of the liver segment prior to transplantation showed that the hepatocytes stained positively for the HBV surface protein (HBsAg) (FIG. 3B). After transplantation, evidence was provided for the human origin of the transplanted cells by using staining with periodic acid-Schiff reaction which identifies glycogen in human hepatocytes (FIG. 3C). 19 days after transplantation, the subcapsular area of the SCID-BNX chimera kidney was immunohistologically stained and HBsAg was detected in discrete areas of the cytoplasm in the engrafted tissue but not in the neighboring mouse kidney cells (FIG. 3D).

Example 3
Transplantation of Liver Fragments Infected in vitro with HBV

Liver fragments were obtained from non HBV infected humans as described in Example 1. The non infected human liver fragments were incubated in vitro with HBV resulting in their infection by HBV. The in vitro HBV infected liver fragments were transplanted under the kidney capsule of SCID-BNX mice as described in Example 1 and the detection of HBV in the transplanted mice was assessed either by immunohistology of the hepatocytes as described in Example 2) or by testing the level of HBV in the serum of the mice by reverse transcriptase-nested-polymerase chain reaction (RT-PCR) as follows:

RNA was dissolved in 10 μl RNAase-free water. cDNA was synthesized using 50 ng of the antisense primer ASI in a reaction mixture containing 2×Taq polymerase buffer (Promega Corp., Madison, Wis.) 0.5 mM dNTP, 20 units RNAsin (Promega), 10 mM dithiothreitol and 30 units avian myeloblastosis virus reverse transcriptase (Life Sciences, Bethesda, Md.) for 60 min. at 42° C. PCR was performed in reaction mixture volume of 50 μl containing Taq Polymerase buffer (Promega), 2 mM dNTP, 1.5 mM $MgCl_2$, 20 ng of sense primer SI and 2.5 units Taq Polymerase (Promega). The reaction was carried out by 35 cycles of PCR consisting of 94° C. for 1.5 min. 55° C. for 1.5 min. and 72° C. for 3 min. The second PCR reaction was performed as before, with 5 μl of the first PCR reaction mixture and the nested set of primers SII (sense) and ASII (antisense). The two sets of primers used are from the highly conserved 5' untranslated region (5' UTR).

The following primers were used:

SI 7-26 (SEQ ID NO:1): 5'-CAC-TCC-ACC-ATA-GAT-CAT-CCC-3'.

ASI 248-222 (SEQ ID NO:2): 5'-ACC-ACT-ACT-CGG-CTA-GCA-GT-3'

SII 46-65 (SEQ ID NO:3): 5'-TTC-ACG-CAG-AAA-GCG-TCT-AG-3'.

ASII 190-171 (SEQ ID NO:4): 5'-GTT-GAT-CCA-AGA-AAG-GAC-CC-3'.

The results are shown in the following Table 2:

capsule of SCID-BNX mice as described in Example 1. The presence and level of HCV in the serum of the transplanted mice was assessed by reverse transcriptase-nested-polymerase chain reaction (RT-PCR) as described in Example 3 above.

The results obtained following transplantation of HCV infected liver fragments shown in the following Table 3:

TABLE 3

Transplantation results of liver fragments from HCV infected human patients in SCID-BNX mice
Number of Mice

| Transplanted with HCV-infected liver fragments | Surviving | Stably Engrafted | Viremia positive |
|---|---|---|---|
| 20 | 17 | 15 | 8 |
| 17 | 14 | 10 | 7 |
| 13 | 11 | 6 | 5 |
| 12 | 10 | ND* | 6 |

*ND = No Data: mice have not yet been sacrificed for histological examination

Figure 4A:
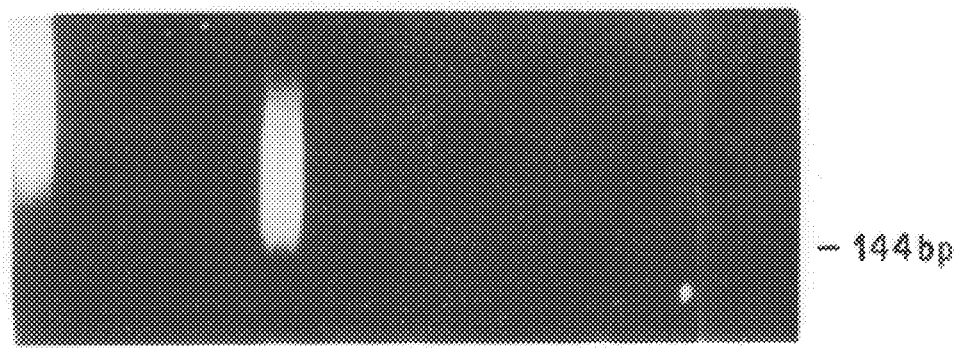
FIGS. 4A–4B are an electrophoretogram of cDNA of RNA samples extracted from sera of SCID-BNX chimera, transplanted under the kidney capsule with human liver infected with HCV, and subjected to RT-PCR amplification using two sets of primers as described in Example 3. Each lane represents a different mouse which was sacrificed at the day of sampling. The first 13 lanes, which are shown at the upper part of FIG. 4, are from mice at day 9 after transplantation. The remaining lanes are from days 14–53 after transplantation (the days are indicated above the lanes). The last two lanes are negative control (−) and positive control (+).
Figure 4B:
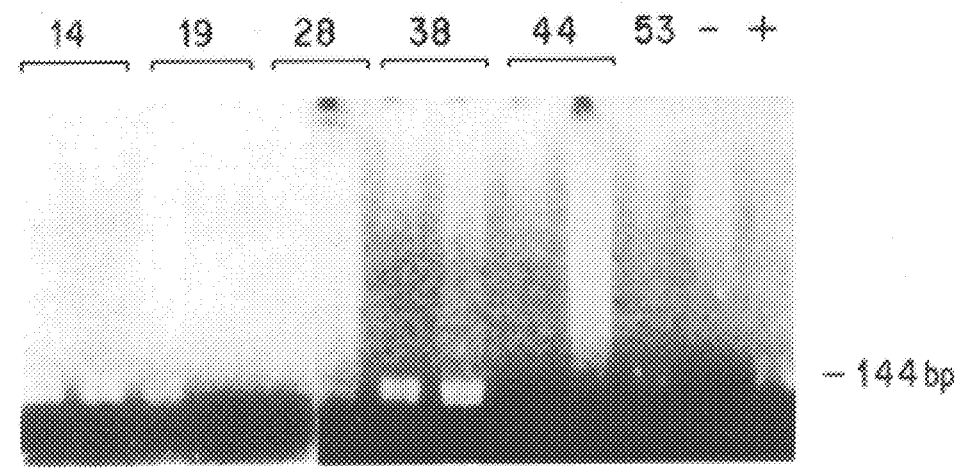

HCV sequences were first observed in the sera of the transplanted mice two weeks post transplantation and continued to be detected intermittently for about two months after transplantation, at which time animals were sacrificed (a typical experiment is shown in FIG. 4). Similar fluctuations in detection of the HCV RNA have been previously observed in chimpanzees experimentally infected with HCV and in chronically infected patients, probably resulting from the very low levels of the virus in the serum.

Example 5
Transplantation of Liver Fragments Infected in vitro with HCV to C3H Mice C3H mice, which are not of an immune deficient strain, were irradiated by split total body irradiation (TBI) (a first dose of 400 rads and a second dose of 1,200 rads) and radioprotected the following day with $3 \times 10^6$ SCID bone marrow cells (as described in Example 1 above).

TABLE 2

Transplantation Results of in vitro Viral Hepatitis B Infected Human Livers in SCID-BNX Mice

| No. of Animals | No. of Animals Survived | No. of Animals Engrafted | Route of Infection* | Infection Indicators and comments** |
|---|---|---|---|---|
| 10 | 5 | 5 | Pre-transplantation in vitro incubation of liver fragments with HBV-DNA, +ve sera | PCR +ve (3/5) |
| 10 | 7 | ND*** | Pre-transplantation in vitro incubation of liver fragments with HBV-DNA, +ve sera | PCR +ve 1/7 at day 11 PCR +ve 4/7 at day 30 |
| 10 | 5 | ND | Pre-transplantation in vitro incubation of liver fragments with HBV-DNA, +ve sera | PCR +ve 1/5 at day 11 |

*+ve sera = sera positive for viremia
**PCR +ve = PCR test positive for hepatitis virus DNA
***ND = No Data: Mice have not yet been sacrificed for histological examination.

As seen in the above table, HBV sequences were observed in the sera of some of the transplanted mice about ten days after transplantation and with progression of time after transplantation HBV sequences were observed in a larger number of transplanted mice.

Example 4
Detection of HCV in sera of mice transplanted with liver fragments from HCV infected patients Liver fragments from three patients with chronic HCV infection were obtained and transplanted under the kidney Liver fragments were obtained from non HCV infected humans as described in Example 1 and the non infected human liver fragments were incubated in vitro with HCV resulting in their infection by HCV. The in vitro HCV infected liver fragments were transplanted under the kidney capsule of the C3H mice as described above and the detection of HCV in the transplanted mice was assessed by testing the level of HCV in the serum of the mice by RT-PCR as described in Example 3 above.

The results are shown in the following Table 4:

TABLE 4

Transplantation Results of in vitro Viral Hepatitis C Infected Human Livers in C3H Mice

| No. of Animals | No. of Animals Survived | No. of Animals Engrafted | Route of Infection | Infection Indicators and comments*** |
|---|---|---|---|---|
| 10 | 10 | ND* | Pre-transplantation in vitro incubation of liver fragments with HCV-DNA, +HCV sera** | PCR +HCV 2/10 at day 14 |

*ND = No Data: Mice have not yet been sacrificed for histological examination
**+HCV sera = sera positive for HCV
***PCR +HCV = PCR test postitive for hepatitis C virus DNA.

The results shown in the table above, demonstrate for the first time, that human liver fragments infected in vitro with HCV may be engrafted and result in the infection of the transplanted mice with HCV as assessed by the detection of HCV sequences in the sera of the transplanted mice.

In addition, the above results, for the first time, show that human HCV infected livers may be transplanted under the kidney capsules of C3H mice, which are not of an immune deficient strain.

---

I claim:

1. A method for evaluating the potential of an agent or a combination of agents in therapy of a hepatitis virus (HV) infection, comprising:
   (a) providing a chimeric mouse or rat M5 having xenogeneic cells; said chimeric mouse or rat M5 being a mouse or rat M1 treated to substantially destroy its hematopoietic cells and then transplanted with hematopoietic cells from one or more mice M2 harboring a defect in T- and B-cell production and transplanted with liver tissue from a xenogeneic mammal M3 of a species capable of being infected by HV; the xenogeneic liver tissue in the mouse or rat M5 being infected by HV;
   (b) administering said agent or said combination of agents to said mouse or rat M5; and
   (c) evaluating the effectiveness of said agent or said combination of agents in preventing spread of HV infection or reducing its physiological symptoms in said mouse or rat M5.

2. A method according to claim 1, wherein the hematopoietic cells of said mouse or rat M1 are substantially destroyed by total body irradiation (TBI).

3. A method according to claim 2, wherein the irradiation is a split total body irradiation (TBI).

4. A method according to claim 1, wherein at least one of said mice M2 is a severe combined immuno-deficient (SCID) mouse.

5. A method according to claim 1, wherein said M3 mammal is an HBV or HCV infected mammal.

6. A method according to claim 5, wherein the HBV or HCV infected mammal M3 is a human hepatitis patient.

7. A method according to claim 1, wherein said M3 mammal is a non-HV infected mammal and the liver tissue is infected with HV in vitro prior to transplantation thereof into the mouse or rat M1.

8. A method according to claim 1, wherein said M3 mammal is a non-HV infected mammal, and the mammal obtained after transplantation (M4) is inoculated with HV.

9. A method for evaluating the potential of an agent or a combination of agents, in prevention of a hepatitis virus (HV) infection, comprising:
   (a) providing a chimeric mouse or rat M4, being a mouse or rat M1, treated to substantially destroy its hematopoietic cells and then transplanted with hematopoietic cells from one or more mice M2 harboring a defect in T- and B-cell Production and transplanted with non-HV infected liver tissue from a xenogeneic mammal M3 of a species capable of being infected by HV;
   (b) administering said agent or said combination of agents to said mouse or rat M4;
   (c) infecting said mouse or rat M4 with HV; and
   (d) evaluating the effectiveness of said agent or said combination of agents in preventing primary HV infection of said xenogeneic liver tissue.

10. A method according to claim 9, wherein the hematopoietic cells of said mouse or rat M1 are substantially destroyed by total body irradiation (TBI).

11. A method according to claim 10, wherein the irradiation is a split total body irradiation (TBI).

12. A method according to claim 9, wherein at least one of said mice M2 is a severe combined immuno-deficient (SCID) mouse.

* * * * *